United States Patent [19]
Thead et al.

[11] Patent Number: 6,158,314
[45] Date of Patent: Dec. 12, 2000

[54] METHOD AND APPARATUS FOR DISABLING AND DISPOSING OF A SINGLE-USE HYPODERMIC SYRINGE

[75] Inventors: William H. Thead; David R. Thead; John C. Evans, all of Atlanta, Ga.

[73] Assignee: Post Medical, Atlanta, Ga.

[21] Appl. No.: 09/182,169

[22] Filed: Oct. 29, 1998

[51] Int. Cl.[7] ................................ B26D 7/06
[52] U.S. Cl. ................... 83/23; 83/607; 30/124
[58] Field of Search ............... 83/944, 607, 597; 30/124, 131

[56] References Cited

U.S. PATENT DOCUMENTS

| | | | |
|---|---|---|---|
| 3,404,593 | 10/1968 | Arcarese et al. | 83/167 |
| 3,469,750 | 9/1969 | Vanderbeck | 225/94 |
| 3,683,733 | 8/1972 | Johan et al. | 83/199 |
| 3,785,233 | 1/1974 | Robinson | 83/167 |
| 4,035,911 | 7/1977 | Nethercutt et al. | |
| 4,255,996 | 3/1981 | Choksi et al. | 83/140 |
| 4,275,628 | 6/1981 | Greenhouse. | |
| 4,315,448 | 2/1982 | Ball. | |
| 4,375,849 | 3/1983 | Hanifl | 206/366 |
| 4,576,281 | 3/1986 | Kirksey. | |
| 4,614,035 | 9/1986 | Andrews. | |
| 4,798,587 | 1/1989 | Willoughby. | |
| 4,867,309 | 9/1989 | Germain. | |
| 5,069,667 | 12/1991 | Freundlich et al. | |
| 5,091,621 | 2/1992 | Butler | 219/68 |
| 5,163,375 | 11/1992 | Withers et al. | 110/346 |
| 5,259,501 | 11/1993 | Withers et al. | |
| 5,322,164 | 6/1994 | Richardson et al. | |
| 5,573,113 | 11/1996 | Shillington et al. | |
| 5,588,966 | 12/1996 | Atsumi. | |
| 5,630,506 | 5/1997 | Thorne et al. | |
| 5,736,706 | 4/1998 | Butler | 219/68 |

*Primary Examiner*—Lee Young
*Assistant Examiner*—Kevin G. Vereene
*Attorney, Agent, or Firm*—Pitts & Brittian

[57] ABSTRACT

A method and an apparatus for disabling and disposing of a single-use hypodermic syringe from re-use by severing the syringe barrel above the syringe needle and collecting the severed portion of the barrel, including the syringe needle directly in an associated, puncture-resistant receiving receptacle. The apparatus includes a severing means having an opening for receiving at least that end of the syringe having a needle attached thereto and a syringe stop for delimiting the passage of the syringe into the opening and stabilizing the syringe in the opening as the syringe barrel is severed from the syringe above the syringe needle, and a collection receptacle having an open end adapted for receiving the severing means and for collecting the severed portion of the syringe barrel including the syringe needle directly therein. The severing means includes a severing mechanism for severing the syringe barrel from the syringe above the syringe needle and an actuating mechanism for actuating the severing mechanism to sever the barrel of the syringe above the needle. The method for disabling and disposing of a syringe needle from a single-use hypodermic syringe using this apparatus includes the steps of inserting the syringe into the syringe receiving opening until the syringe barrel hub abuts the syringe stop, rotating the actuating mechanism to sever the syringe barrel from the syringe above the syringe needle, and collecting the severed portion of the syringe barrel, including the needle attached thereto in the collection receptacle.

10 Claims, 6 Drawing Sheets

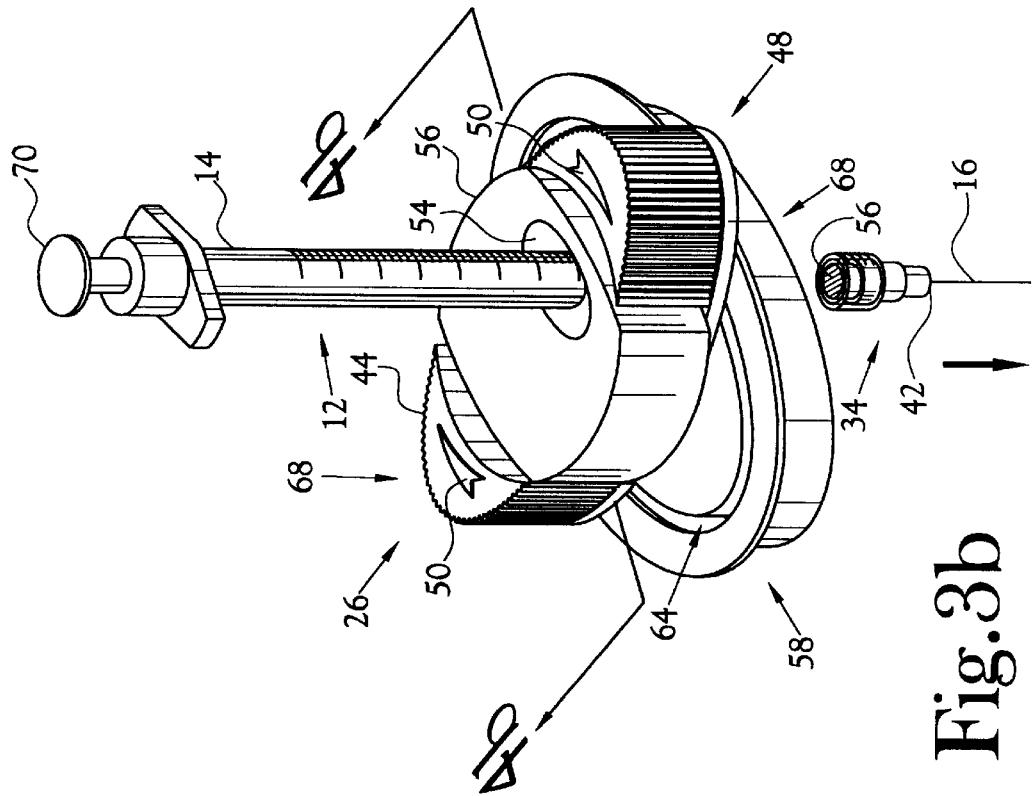
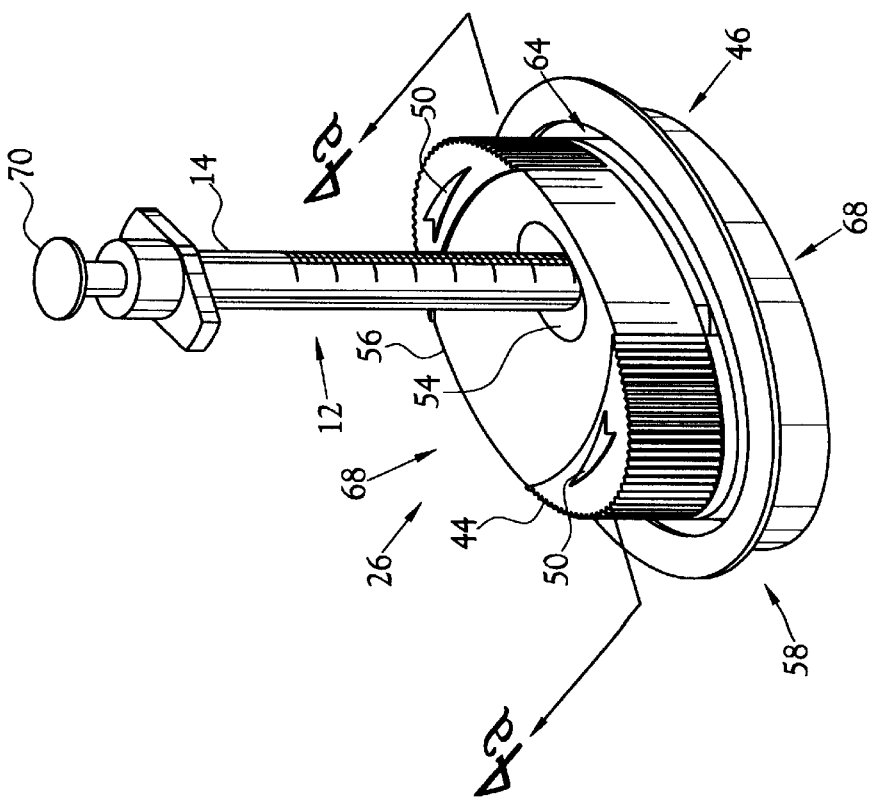
Fig. 3b
Fig. 3a

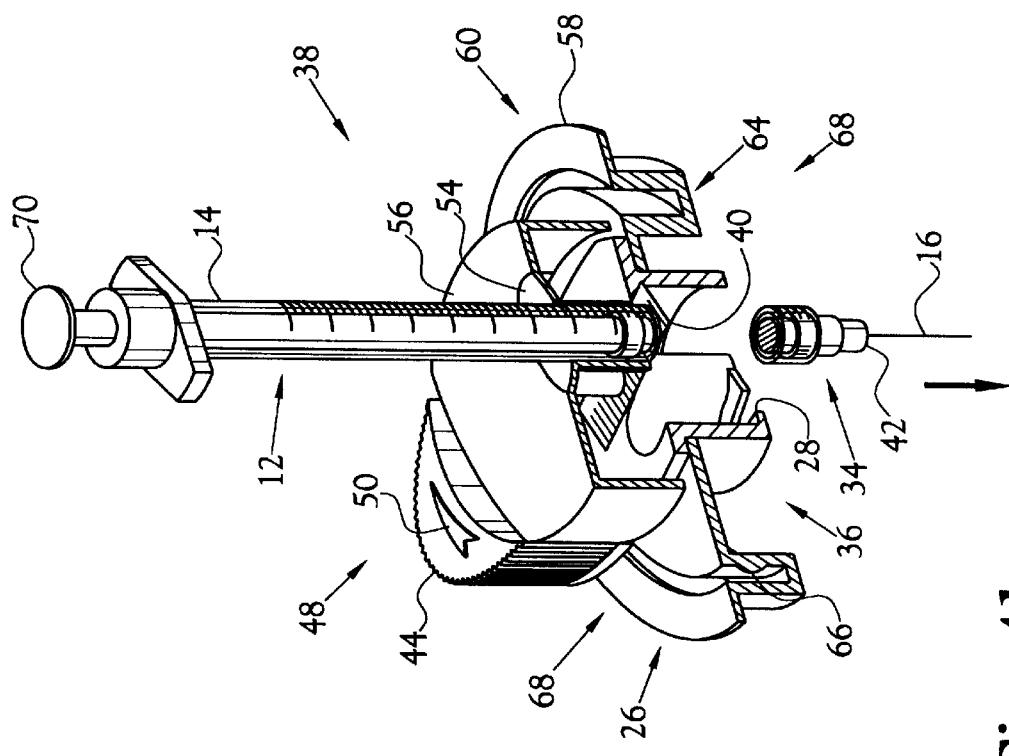
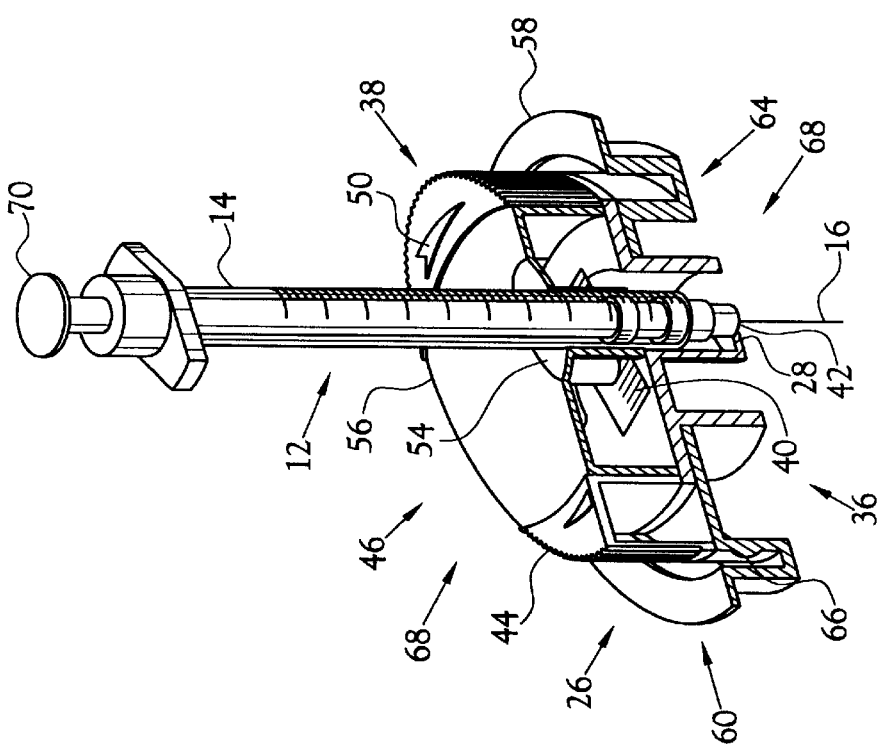

METHOD AND APPARATUS FOR DISABLING AND DISPOSING OF A SINGLE-USE HYPODERMIC SYRINGE

TECHNICAL FIELD

This invention relates to the field of medical devices and those devices used to extract and dispose of bio-hazardous wastes such as used syringes and syringe needles. More particularly, this invention relates to a method and apparatus for disabling and disposing of a single-use hypodermic syringe such as is used to treat medical conditions including diabetes and tuberculosis.

BACKGROUND ART

A hypodermic syringe typically includes a barrel having a hub, a plunger slidably received in the barrel and a syringe needle positioned on the barrel hub. Hypodermic syringes are essential tools for a health care provider's treatment of their patients. Single-use hypodermic syringes are particularly important to individuals who self-medicate in a home setting to control medical conditions such as diabetes.

Single-use needles in the art are typically integrally formed with the syringe barrel hub or are separate components which are removably secured to the barrel hub. Where removable, the syringe needle typically includes a plastic collar having an interior surface which is connected or friction fit onto the hub of the syringe and an exterior surface which includes a series of equidistantly spaced splines to assist in grasping and removing the needle. The more common connectors include screw, LUER-LOK®, and LUER-SLIP™ connectors. In use, the needle is typically either inserted into a medication vessel to obtain a dosage of medication to be administered to a patient or inserted into the patient to withdraw and evaluate a fluid sample. Thereafter, the hypodermic syringe is discarded either in its entirety or after the syringe needle is somehow separated from the syringe.

Proper syringe disposal has become a primary health concern as a result of the recent rise in the number and type of diseases carried by human bodily fluids and the increasing incidence of discarded syringes being reclaimed for illegal drug use. In the past, a diabetic patient in a home environment, for example, could dispose of used insulin syringes, including their needles, by collecting the syringe and attached needle in a container, such as a milk, bleach, or other similar container, and discarding the container in the regular household trash when the container was filled. Now, it is neither safe nor practical to dispose of such syringes in household trash cans as they have become fertile supply sources for those who seek syringes and their needles for their illicit drug use. The easiest and most effective way to insure the proper and final disposal of such syringes is to disable them from re-use.

Other devices have been produced to disable or dispose of used syringes and syringe needles. However, the prior art discloses devices which only separate the syringe needle from the syringe barrel hub and, consequently, fail to disable the syringe from re-use. Both the syringe barrels and the needles therefore, are available for retrieval and re-use.

U.S. Pat. No. 4,614,035, issued to Andrews, discloses a needle removing device which severs the syringe needle from the syringe hub along a length of the syringe needle shaft. However, the Andrews device fails to permanently disable the syringe barrel as its re-use is enabled by removing the needle hub after having severed the needle tip from the syringe hub, and replacing it with another syringe needle.

U.S. Pat. No. 4,035,911, issued to Nethercutt, et al., discloses a needle severing device which is repeatedly sanitized and reused in clinical settings. The Nethercutt device severs a substantial portion of the syringe barrel and syringe needle from the syringe. A removable receptacle collects the severed waste until the receptacle is filled and emptied. The Nethercutt device is designed and intended for re-use. In use, it places the user at risk of exposure to the air-borne fluid particulate that results from the severing of the syringe in an open environment. The Nethercutt device also exposes the user to the risk of injury or contamination arising from handling of the storage receptacle which is full of severed needles and mixed waste fluids and must be emptied.

U.S. Pat. No. 4,275,628, issued to Greenhouse, discloses a device for severing a syringe needle having disadvantages similar to those of the Nethercutt device. The Greenhouse device includes a severing mechanism which severs a substantial portion of the syringe hub from the syringe barrel at the same time that it severs the syringe needle and collects the severed syringe portions in a collecting receptacle. This device fails to insulate the user from exposure to airborne fluid particulate resulting from the severing process and places the user at risk of injury in the event that the device falls and contaminated shreds of needle or needle hub escape from an unprotected opening in the collecting receptacle. Moreover, the Greenhouse device comprises a complicated and costly operating mechanism and is not readily disposable.

U.S. Pat. No. 4,315,448, issued to Ball, discloses a wall-mounted needle extraction unit which requires a user to hold a used syringe in a perpendicular position with respect to the wall-mounted device while the other hand operates the device. The Ball device is disposed in a wall unit and exposes the user to the risks inherent in emptying the collection unit, such as spillage and inadvertent needle sticks, or the risks incident in retrieving those spilled needles. The Ball device fails to protect the user from the risk of exposure to the airborne fluid particulate created as a result of the severing process. It is neither portable nor readily disposable. Moreover, it fails to contemplate disabling the used syringe barrel from re-use. Rather, like the device of the '035 patent to Andrews, the Ball device focuses exclusively on shearing the needle from the syringe.

Therefore, it is an object of this invention to provide a method and an apparatus for disabling a single-use hypodermic syringe such as an insulin syringe or a tuberculin syringe from re-use by severing the syringe barrel above the syringe needle.

It is also an object of this invention to provide an apparatus for disabling a single-use syringe that provides a severing mechanism disposed within an enclosed area to minimize the conveyance of air-borne fluid particulate which may be created during the severing process and protect the user from the risks of exposure to that particulate.

Moreover, it is an object of the present invention to provide a method and an apparatus for disabling and disposing of a single-use syringe wherein an operator's insertion of a syringe into a syringe receiving opening and rotation of an actuating mechanism initiates displacement of a severing device to sever the syringe barrel from the syringe and allow for the collection of the severed portion of the syringe barrel, including the syringe needle, in a receiving receptacle pending disposal.

It is an object of the present invention to provide a method and an apparatus for disabling and disposing of a single-use hypodermic syringe whose concepts are specifically adapted for disabling and disposing of varying types of single use syringe needles such as tuberculin or insulin syringes.

Another object of the present invention is to provide a method and an apparatus for disabling and disposing of a single-use syringe which provides a syringe receiving opening that is closed when the apparatus is not in use to prevent the inadvertent escape of the stored, severed syringe barrels.

Yet another object of the present invention is to provide a method and apparatus for disabling and disposing of a single-use hypodermic syringe wherein the receiving receptacle and receptacle cover are integrally formed to preclude spillage of waste or waste fluid such that the apparatus may be shipped to and disposed of by a selected facility for disposing of such wastes.

DISCLOSURE OF THE INVENTION

Other objects and advantages will be accomplished by the present invention which provides a method and an apparatus for disabling and disposing of a single-use hypodermic syringe from re-use by severing the syringe barrel above the syringe needle and collecting the severed portion of the barrel, including the syringe needle, directly in an associated receiving receptacle. When the receptacle is full, it and its contents are readily disposed of without exposure of users or sanitation personnel to its contents.

The apparatus for disabling and disposing of a single-use hypodermic syringe includes a severing means having an opening for receiving at least that end of the syringe having a needle attached thereto and a syringe stop for delimiting the passage of the syringe into the syringe receiving opening, a severing mechanism for severing the syringe barrel at a location above the syringe needle and a collection receptacle adapted to receive the severing means and to collect the extracted portion of the syringe barrel including the syringe needle directly therein. The severing means includes a severing mechanism for severing the syringe barrel from the syringe above the syringe needle and an actuating mechanism for actuating operation of the severing mechanism to sever the barrel of the syringe above the needle. The syringe stop and the syringe receiving opening cooperate with the severing means to stabilize the syringe in the syringe receiving opening during the severing and disabling process. The syringe stop also provides a barrier to prevent spillage of severed syringe needles from the receiving receptacle.

The apparatus for disabling and disposing of a single-use hypodermic syringe preferably includes a disposal cover which is removably friction fit about the severing means when the severing means is not in use and is non-removably snap fit about the severing means when the collection receptacle is filled and ready for disposal. The apparatus for disabling and disposing of a single-use hypodermic syringe preferably is adapted to disable and dispose of single-use diabetic syringes.

A method for disabling and disposing of a single-use hypodermic syringe by severing the syringe above the syringe needle includes the steps of inserting the syringe into the syringe receiving opening of the severing mechanism until the hub of the syringe barrel abuts the syringe stop; rotating the actuating mechanism to sever the syringe barrel from the syringe at a location above the syringe needle so that the severed barrel and the syringe needle are collected in the receiving receptacle; restoring the actuating mechanism to its original position; and, removing and disposing of that portion of the syringe barrel remaining in the syringe receiving opening. These steps are repeated until the receiving receptacle is filled, whereafter the steps of placing the disposal cover about the severing mechanism and applying a greater than usual force to the disposal cover to non-removably secure it about the severing means to prepare the apparatus for proper disposal. The method optionally further includes the steps of removing the disposal cover from about the severing means; placing the disposal cover, open end first, about the closed end of the receiving receptacle prior to use of the apparatus and removably replacing the disposal cover about the severing means when the apparatus is completed.

BRIEF DESCRIPTION OF THE DRAWINGS

The above mentioned features of the invention will become more clearly understood from the following detailed description of the invention read together with the claims and drawings in which:

FIG. 3a and 3b show isometric views of the two operational positions of the apparatus for disabling and disposing of a single-use hypodermic syringe illustrated in FIGS. 2a and 2b, respectively;

FIGS. 4a and 4b are perspective views, partially sectioned, of the extraction mechanism of the apparatus for disabling and disposing of a single-use hypodermic syringe taken generally along the line 4a—4a of FIG. 3a and generally along the line 4b—4b of FIG. 3b, respectively;

BEST MODE FOR CARRYING OUT THE INVENTION

Figure 1:
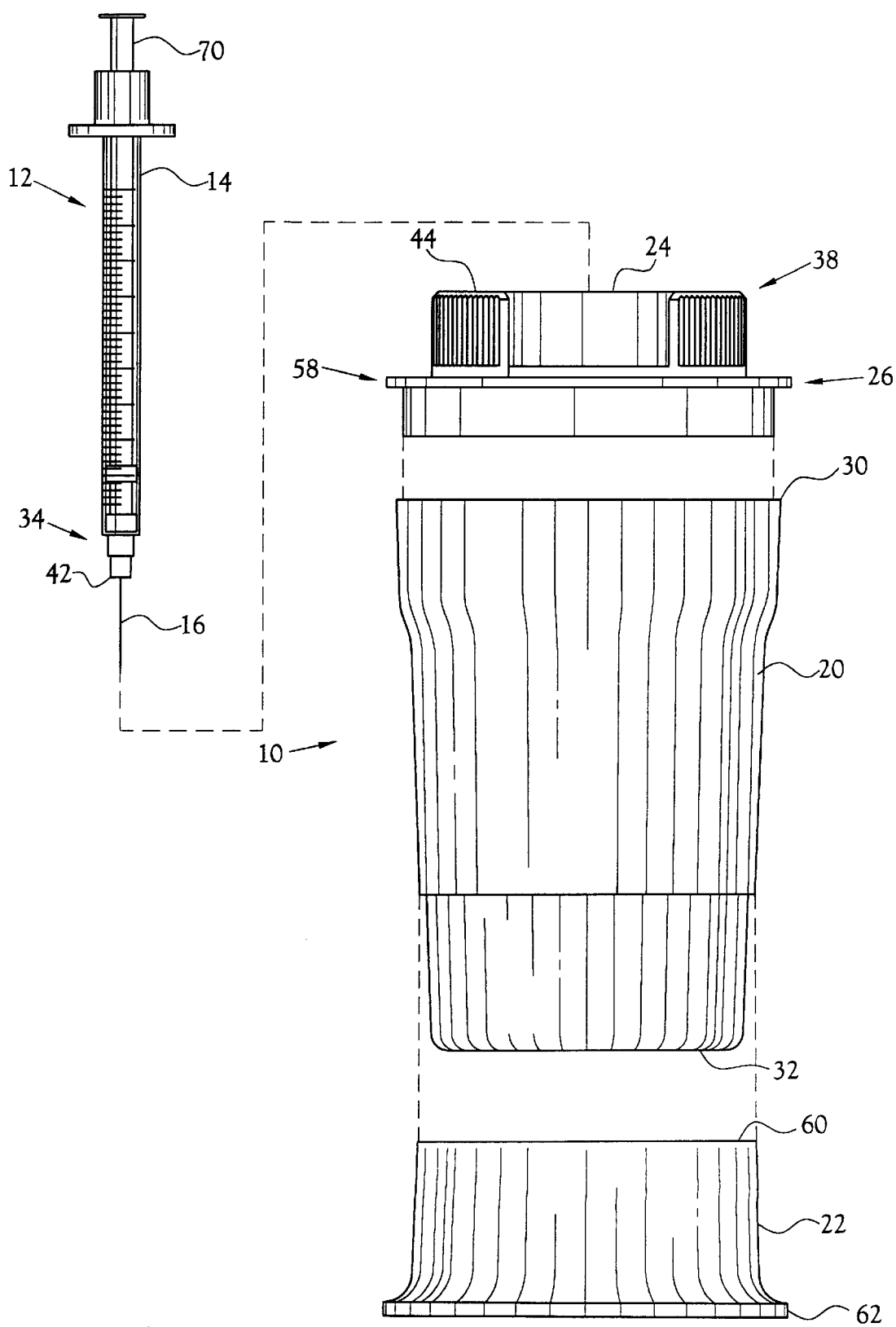
FIG. 1 is a side elevation view of the apparatus for disabling and disposing of a single-use hypodermic syringe constructed in accordance with several features of the present invention.
Figure 2A:
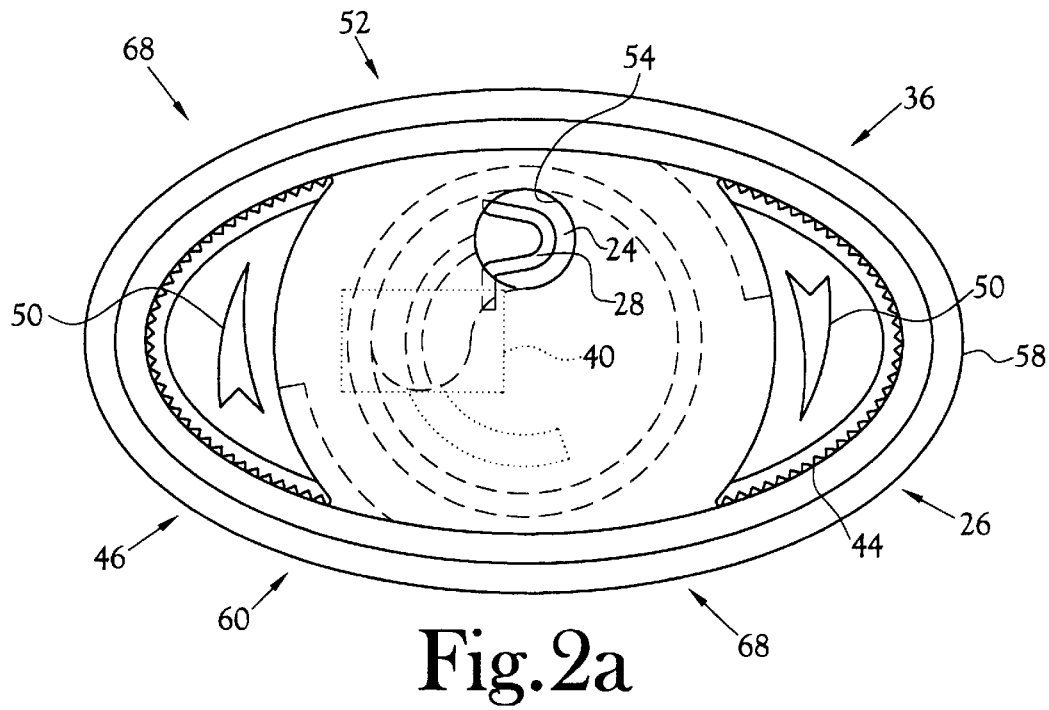
FIGS. 2a and 2b illustrate a plan top view of the apparatus for disabling and disposing of a single-use hypodermic syringe at two different operating positions.
Figure 2B:
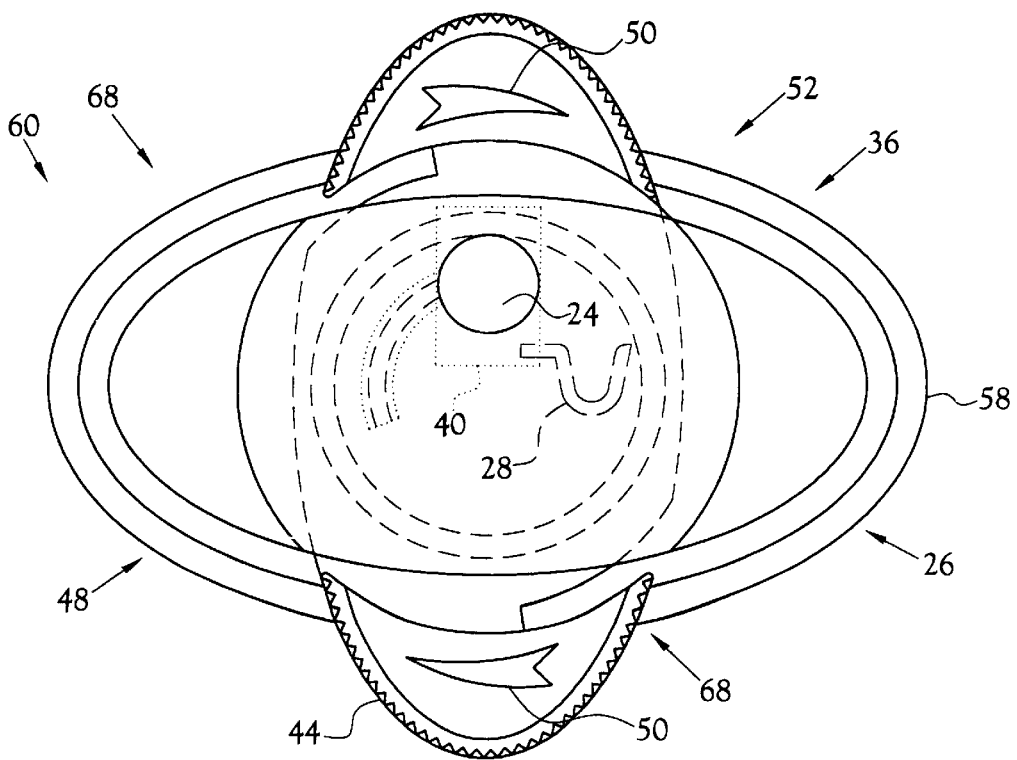

An apparatus for disabling and disposing of a single-use hypodermic syringe incorporating various features of the present invention is illustrated generally at 10 in the figures. As illustrated in FIG. 1, a single-use hypodermic syringe 12 includes a syringe barrel 14 having a barrel hub 34, a plunger 70 slidably received in the barrel 14 and a syringe needle 16 integrally formed with or removably secured to the hub 34 of the syringe barrel 14. The apparatus for disabling and disposing of a single-use hypodermic syringe 10 disables a single-use syringe 12 from re-use by severing the syringe barrel 14 above the syringe needle 16 and collecting the severed portion of the barrel 14, including the syringe needle 16, in an associated receiving receptacle 20 until the receptacle 20 is full and the apparatus 10 is ready for disposal. The apparatus for disabling and disposing of a single-use hypodermic syringe 10 of the preferred embodiment further includes a disposal cover 22 which removably covers the apparatus 10 when it is not in use and non-removably seals the apparatus 10 when the receiving receptacle 20 is filled and ready for disposal.

As shown in FIGS. I and 2, the apparatus for disabling and disposing of a single-use hypodermic syringe 10 includes a severing means 26 having a syringe receiving opening 24 for receiving and severing at least that end of a single-use hypodermic syringe 12 having a syringe needle attached thereto and a syringe stop 28 for delimiting the passage of the syringe 12 in the syringe receiving opening 24, and a receiving receptacle 20 having an open end 30 for receiving the severing means 26 and directly collecting the severed portion of the syringe barrel 14 including the syringe needle directly therein until the receptacle 20 is filled and the apparatus 10 is ready for disposal. The receiving receptacle 20 includes a closed end 32 opposite the open end 30. In operation, the syringe stop 28 and the syringe receiving opening 24 cooperate with the severing means 26 to stabilize the single-use syringe 12 in the syringe receiving opening 24 as a portion of the syringe barrel 14 above the syringe needle 16 is severed from the syringe 12.

The apparatus for disabling and disposing of a single-use hypodermic syringe 10 of the preferred embodiment disables and disposes of single-use diabetic syringes such as those manufactured by Becton-Dickinson and Kendall, Sherwood, Davis & Geck. Those skilled in the art will readily foresee that an apparatus for disabling and disposing of a single-use hypodermic syringe 10 such as the present invention is easily adaptable to provide a device for disabling and disposing of other specific types of single-use syringes, such as tuberculin syringes.

As illustrated in FIGS. 3 and 4, the severing means 26 includes a severing mechanism 36 for severing a portion of the syringe barrel 14 above the syringe needle 16 from the syringe 12 and an actuating mechanism 38 for imparting a force on the severing mechanism 36 to operate the severing mechanism 36. In the preferred embodiment, the actuating mechanism 38 is disposed about the needle receiving opening 24 and assists in defining a path of movement which is coordinated with that of the severing mechanism 36 such that the actuating mechanism 38 is in a first position 46 when the single-use syringe 12 is inserted into the syringe receiving opening 24 and rotation of the actuating mechanism 38 causes the rotation of the severing mechanism 36 to a second position 48 to sever at least that end of the syringe barrel 14 above the syringe needle 16 from the single-use syringe 12. The severing mechanism 36 of the preferred embodiment is a sharp cutting instrument, such as a razor blade 40. The actuating mechanism 38 of the preferred embodiment is a knob 44 having indicators 50 which indicate the proper direction for manipulation of the knob 44 and operation of the apparatus 10.

As also illustrated in FIGS. 3 and 4, in the preferred embodiment, the actuating mechanism 38 and severing mechanism 36 are coordinately rotated one-quarter turn in a clockwise direction to sever the syringe barrel and one-quarter turn in a counter-clockwise direction to restore the mechanisms 36, 38 to their original position. The coordinated rotation of the mechanisms 36, 38 in a quarter turn rotation enables the user to more readily appreciate when the severing process is completed. Other methods of indicating completion of the severing process are also foreseeable. Though not illustrated, the apparatus for disabling and disposing of a single-use hypodermic syringe 10 is also adaptable to be fitted with a biasing device for biasing the actuating mechanism 38 in the first position to receive the syringe 12 and return the actuating mechanism 38 to the first position 46 after it has been rotated to the second position 48 to sever the syringe barrel 14 from the syringe 12.

In the preferred embodiment, the apparatus for disabling and disposing of a single-use hypodermic syringe 10 disables and disposes of single-use diabetic hypodermic syringes having dosage capacities of up to 1 cc. As those skilled in the art will understand, the apparatus 10 of the preferred embodiment severs a greater portion of the syringe barrel above the syringe needle of syringes having a smaller dosage capacity and a lesser portion of the syringe barrel of syringes having a higher dosage capacity. In each instance, as illustrated in the drawings, a corresponding lesser or greater portion of the syringe plunger 56 is also severed with the syringe barrel and syringe needle in the severing process. The efficacy of the apparatus 10 in protecting the user from potential exposure to the air-borne fluid particulate that may be created in the severing process remains constant as the difference in the barrel diameter of the syringe being disabled is minimal. In every instance, the syringe receiving opening 24 surrounds the syringe barrel 14 such that the potential exposure to air-borne fluid particulate is minimized, if not eliminated.

Figure 5:
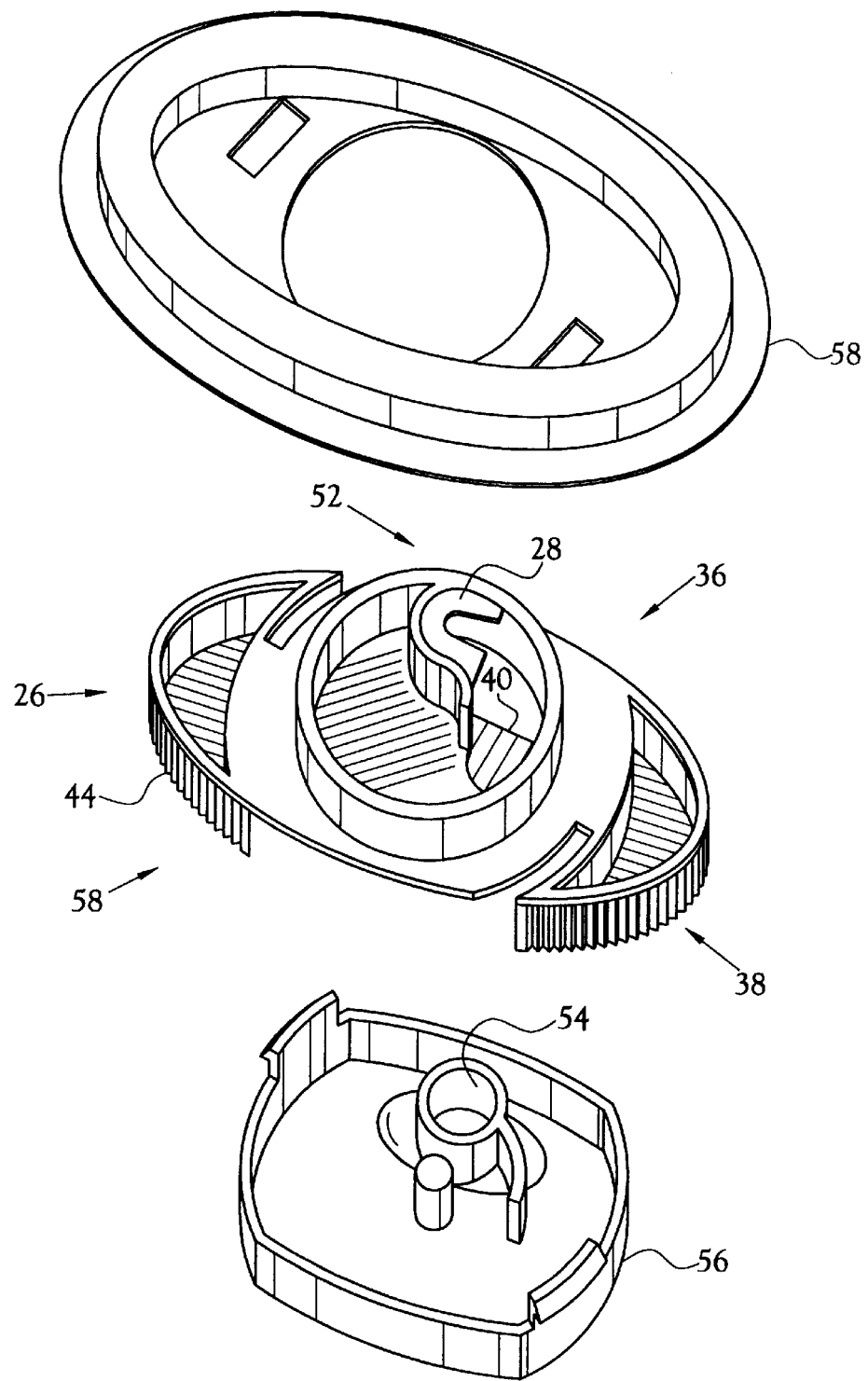
FIG. 5 is an exploded perspective view of the actuating device of the apparatus for disabling and disposing of a single-use hypodermic syringe.

As best illustrated in FIG. 5, the syringe stop 28 has a curvilinear configuration 52 which permits the severed portion of the syringe barrel 14 including the syringe needle 16 to pass directly into the receiving receptacle 20 directly associated with the severing means 26. The relative positioning of the syringe stop 28 and the severing mechanism 36 of the preferred embodiment provides that pressure from the rotational force exerted on the actuating mechanism 38 causes the severing mechanism 36 to stabilize the syringe barrel 14 against the side wall 54 defined by the syringe receiving opening 24 and initiate the severing of that portion of the syringe barrel 14 above the syringe needle 16 just as the syringe hub 34 is slid from the syringe stop 28. As the severing process is completed, the severing mechanism 36 covers the syringe receiving opening 24 and prevents that portion of the hypodermic syringe above the severing mechanism 36 from entering the receiving receptacle 20 as that portion of the syringe barrel 14 having the syringe needle 16 attached thereto is collected in the receiving receptacle 20. In the event that the actuating mechanism 38 is retracted prior to completely severing the syringe 12, the syringe stop 28 coordinately retracts and prevents the syringe 12 from passing through the syringe receiving opening 24. The syringe stop 28 also remains positioned between the syringe receiving opening 24 and the receiving receptacle 20 when the apparatus 10 is not in use to obstruct the receiving opening 24 and avoid the spillage of the severed syringe barrels 14 and attached syringe needles 16 from the receiving receptacle 20.

As may be preferred, but not shown, the syringe needle receiving opening 24 is configurable to include a receiving opening tab disposed along the wall 54 defined by the syringe receiving opening 24. Where provided, the receiving opening tab further stabilizes the syringe inserted into the syringe needle opening 24 and increases the ease of use of the apparatus for disabling and disposing of a single-use hypodermic syringe 10 during the severing process. The tab also heightens user safety by further minimizing the unlikely possibility that the syringe may fall from the syringe receiving opening 24 during operation of the apparatus 10. It also will be recognized that an equally effective manner of accomplishing the security objectives of the receiving opening tab is to contour the dimensions of the syringe receiving opening 24 and the syringe stop 28 according to the dimensions of a single-use hypodermic syringe when it is positioned in the opening 24 and against the stop 28 for severing.

Figure 6:
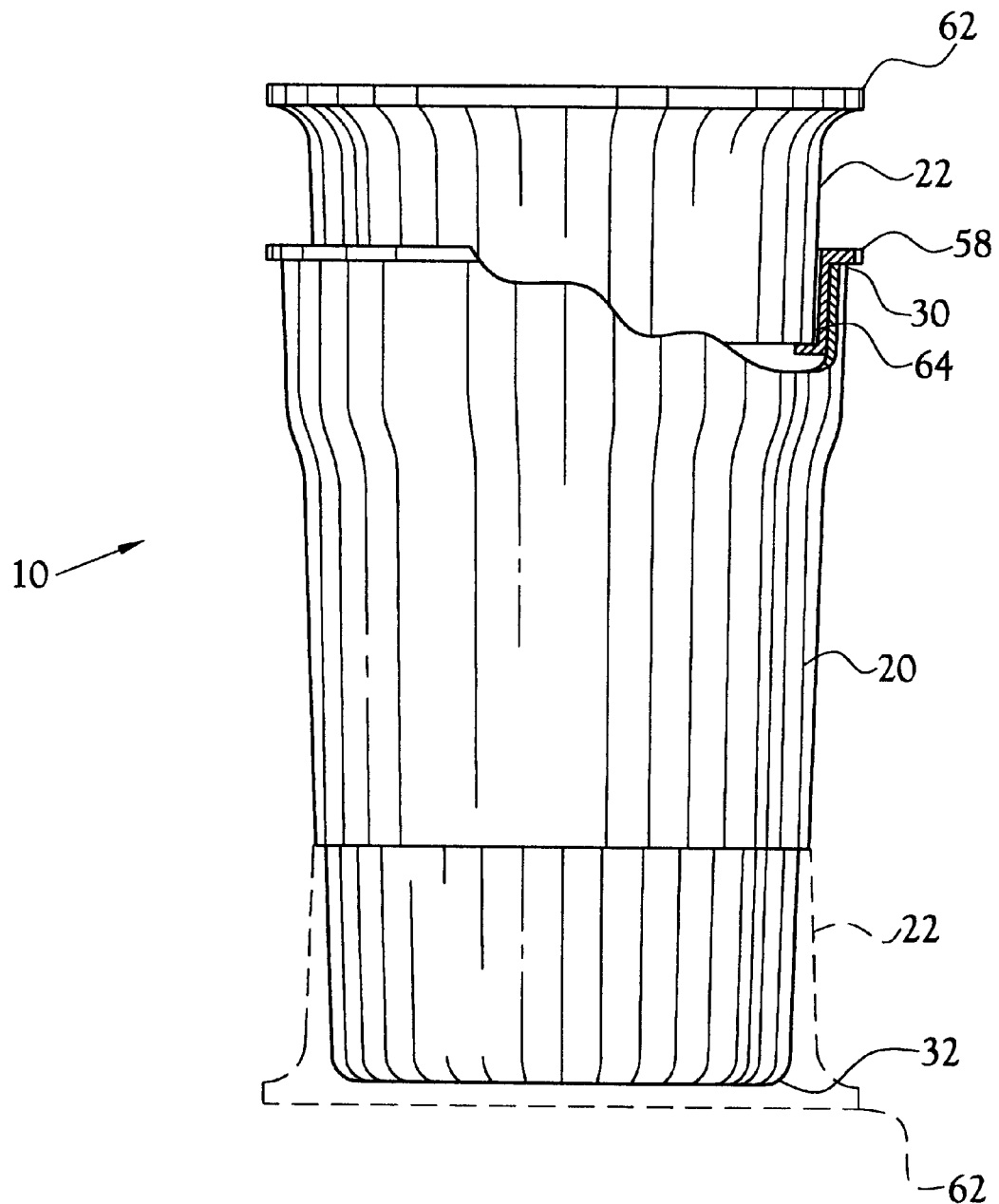
FIG. 6 is a side elevation view of the apparatus for disabling and disposing of a single-use hypodermic syringe.

As shown in FIGS. 5 and 6, in the preferred embodiment, the severing means 26 further defines a receptacle cover 58 adapted to receive the disposal cover 22. The receptacle cover 58 of the preferred embodiment is integrally formed with the receiving receptacle 20 and includes an actuator cover 56 for positioning the actuator mechanism 38 on the receptacle cover 58 and cooperating with the receptacle cover 58 to define the syringe receiving opening 24. The disposal cover 22 includes an open end 60 and a closed end 62 opposite the open end 60. As shown in phantom in FIG. 6, the open end 60 of the disposal cover 22 is dimensioned to be inverted and positioned on the closed end 32 of the receiving receptacle 20 when the apparatus for disabling and disposing of a single-use hypodermic syringe 10 is in use. The open end 60 of the disposal cover 22 is also dimensioned to cover the severing means 26 when the apparatus 10 is not in use and to non-removably secure the severing means 26 when the receiving receptacle 20 is filled and the apparatus 10 is ready for disposal, as also shown in FIG. 6. The closed end 62 of the disposal cover 22 is dimensioned to provide the apparatus for disabling and disposing of a single-use hypodermic syringe 10 with a wider base when it is placed on the closed end 32 of the receiving receptacle 20 and lend greater stability to the operation of the apparatus 10 during operation.

Those skilled in the art will recognize that a receiving receptacle 20 and a disposal cover 22 accomplishing the non-removably sealing objectives of the present invention are attainable in many ways. In one example, not shown, the receiving receptacle 20 defines a periphery that includes at least one set of equally spaced tabs. So long as space remains available in the receiving receptacle 20, the user stores the apparatus for disabling and disposing of a single-use hypodermic syringe 10 by placing the open end 60 of the disposal cover 22 about the severing means 26 such that the open end 60 of the cover 22 abuts, but does not exceed, the tabs. Once the receiving receptacle 20 is filled, the user readies the apparatus 10 for disposal applying a greater than usual pressure on the disposal cover 22 such that the disposal cover 22 is slid over the tabs, and securely and permanently seals the apparatus 10 from access or leakage. In the preferred embodiment illustrated in FIG. 4 and 6, the receptacle cover 58 defines a disposal cover channel 64 and the open end 60 of the disposal cover 22 is friction fit in the disposal cover channel 64 when the apparatus 10 is not in use. The disposal cover channel 64 of the preferred embodiment further includes at least two equally spaced channel tabs 66 which cooperate with the disposal cover 22 to securely seal the unit 10 when the apparatus 10 is filled and the user applies a greater than normal pressure to friction fit the cover 22 into the disposal cover channel 64. Other configurations for covering and sealing the disposal cover 22 about the extraction mechanism 26 are also foreseeable.

Those skilled in the art will also recognize that the receiving receptacle 20 and the disposal cover 22 and associated components of the apparatus for disabling and disposing of single-use hypodermic syringes 10 are particularly configured to provide an ovoid configuration. Other configurations such as round or square are readily foreseeable. However, the ovoid configuration illustrated is preferable as it renders the apparatus for disabling and disposing of single-use hypodermic syringes 10 more readily portable and easier for the user to grasp during use.

It is preferred that the receiving receptacle 20 and the disposal cover 22 and associated components of the apparatus for disabling and disposing of single-use hypodermic syringes 10 are fabricated from puncture-resistant materials to insure user safety as well as the safety of individuals handling the disposed waste. It will be recognized that the non-removable secure sealing of the disposal cover 22 on the receptacle cover 58 is preferred as it precludes access to the discarded needles 16 and severed portions of the syringe barrel 14 attached thereto contained in the receiving receptacle 20. Equally importantly, the non-removable secure sealing of the disposal cover 22 on the receptacle cover 58 is preferred as sealing of the apparatus 10 precludes spillage of any liquid waste collected in the receptacle 20 such that the apparatus 10 can be safely placed in the mail and shipped to an appropriate receiver for proper final disposal.

A method for disabling and disposing of a single-use hypodermic syringe 12 using the herein-described apparatus 10 is now readily understood. The single-use syringe 12 is disabled and disposed of by inserting the syringe 12 into the syringe receiving opening 24 until the syringe hub 34 abuts the syringe stop 28, grasping the receiving receptacle 20 of the apparatus 10 with one hand, applying at least two fingers of the other hand, one each to opposed sides 68 of the knob 44 of the actuating mechanism 38, and using those two fingers to rotate the actuating mechanism 38 approximately one-quarter turn in a clockwise direction, as indicated by the indicators 50 on the actuating mechanism 38. The clockwise rotation of the actuating mechanism 38 causes the razor blade 40 to rotate in a corresponding direction and sever at least a portion of the syringe barrel 14 from the syringe 12 above the syringe needle 16. Counter-clockwise rotation of the actuating mechanism 38 thereafter restores the mechanism 38 to its original position, and that portion of the syringe 12 that remains in the syringe receiving opening 24 is disposed of. This method of use is repeated until the receiving receptacle 20 is filled to a suggested fill line. At that juncture, the apparatus 10 is readied for disposal by placing the open end 60 of the disposal cover 22 in the disposal cover channel 64 and applying a slightly greater than usual pressure to the disposal cover 22 to force the open end 60 of the cover 22 past the channel tabs 66 and non-removably seat the disposal cover 22 in the channel 64 to seal the apparatus 10.

The method further includes the optional steps of removing the disposal cover 22 from the disposal cover channel 64, inverting and positioning the open end 60 of the cover 22 about the closed end 32 of the receiving receptacle 20 prior to using apparatus 10 and restoring the disposal cover 22 about the severing mechanism 34 by removably inserting the open end 60 of the cover 22 in the disposal cover channel 64 when use of the apparatus 10 is completed.

From the foregoing description, it will be recognized by those skilled in the art that an apparatus for disabling and disposing of a single-use hypodermic syringe offering advantages over the prior art has been provided. The apparatus for disabling and disposing of a single-use hypodermic syringe disables the operability of a single-use syringe in a single cutting motion by severing that portion of a syringe barrel above the syringe needle. The apparatus for disabling and disposing of a single-use hypodermic syringe provides a syringe needle remover which is specified for use with a particular single-use needle. Its design, however, is adaptable for the manufacture of devices specified for other types of single-use syringes, such as tuberculin syringes. The severing mechanism is positioned within the severing means to minimize, if not eliminate, user exposure to air-borne fluid particulate that may result from the severing process. The syringe stop and the integral assembly of the severing means with the receiving receptacle preclude inadvertent spillage of the severed syringe barrels and attached syringe needles. The secure sealing of the disposal cover in the disposal cover channel enables the safe and legal mailing of the filled apparatus to appropriate disposal centers. The method for use of the apparatus for disabling and disposing of a single-use hypodermic syringe facilitates the easy, safe and effective disposal of single-use syringes. Moreover, the apparatus for disabling and disposing of a single-use hypodermic syringe enables the user to safely and securely dispose of filled units without fear of their unintended reclamation.

While a preferred embodiment has been shown and described, it will be understood that it is not intended to limit the disclosure, but rather it is intended to cover all modifications and alternate methods falling within the spirit and the scope of the invention as defined in the appended claims.

Having thus described the aforementioned invention, We claim:

1. An apparatus for disabling and disposing of a single-use hypodermic syringe, the syringe including a syringe barrel having a barrel hub, a syringe plunger slidably received in the syringe barrel and a syringe needle integrally formed with or removably secured to the hub of the syringe barrel, said apparatus comprising:

a severing means for severing the syringe barrel, said severing means having a syringe receiving opening for receiving at least a portion of the syringe barrel and a stop for delimiting passage of the syringe barrel through said syringe receiving opening and stabilizing the syringe barrel in said syringe receiving opening, said severing means further having a cutting blade disposed above said stop, whereby the entire syringe needle is removed by severing the syringe barrel without severing the syringe needle, said severing means further including an actuating mechanism for actuating operation of said cutting blade and imparting a force on said cutting blade to securely seat the syringe in said needle receiving opening as the syringe barrel is severed, said actuating mechanism being a knob disposed about said needle receiving opening such that rotation of said knob imparts a horizontal rotational force to said cutting blade to cut the syringe barrel above the syringe needle; and a receiving receptacle having an open end for receiving said severing means and a closed end opposite said open end, said receiving receptacle for receiving and collecting the portion of the syringe barrel severed from the single-use hypodermic needle and the entire needle attached thereto.

2. The apparatus of claim 1 wherein said actuating mechanism further includes a biasing device for reciprocally biasing said knob in a first position wherein said unit is ready to receive the syringe and returning said knob to said first position after said knob has been rotated to a second position to sever the syringe barrel from the syringe.

3. The apparatus claim 1 wherein said stop has a curvilinear configuration which permits the severed portion of the syringe barrel and the syringe needle attached thereto to pass from the stop into said receiving receptacle as it is severed from the syringe.

4. The apparatus of claim 1 further comprising a disposal cover for removably covering said severing means when said apparatus is not in use and non-removably sealing said severing means when said receiving receptacle is filled and said apparatus is ready for disposal, said disposal cover being configured to be inverted and positioned on said closed end of said receiving receptacle to further stabilize said apparatus when said apparatus is in use.

5. The apparatus of claim 4 wherein said severing means further includes a syringe receptacle cover for sealing said receiving receptacle and positioning said actuating mechanism on said syringe receptacle cover, said syringe receptacle cover being configured to cooperate with said disposal cover for removably receiving said disposal cover when said apparatus is not in use and non-removably sealing said severing means when said receiving receptacle is filled and said apparatus is ready for disposal.

6. An apparatus for disabling and disposing of a single-use hypodermic syringe, the syringe including a syringe barrel having a barrel hub, a syringe plunger slidably received in the syringe barrel and a syringe needle integrally formed with or removably secured to the hub of the syringe barrel, said apparatus comprising:

a severing device for severing the syringe barrel, said severing device having a syringe receiving opening for receiving at least a portion of the syringe barrel and a stop for delimiting passage of the syringe barrel through said syringe receiving opening and stabilizing the syringe barrel in said syringe receiving opening, said severing device further having a cutting blade disposed above said stop, whereby the entire syringe needle is removed by severing the syringe barrel without severing the syringe needle, said severing device further including an actuating mechanism for actuating operation of said cutting blade and imparting a force on said cutting blade to securely seat the syringe in said needle receiving opening as the syringe barrel is severed, said actuating mechanism being a knob disposed about said needle receiving opening such that rotation of said knob imparts a horizontal rotational force to said cutting blade to cut the syringe barrel above the syringe needle; and a receiving receptacle having an open end for receiving said severing device and a closed end opposite said open end, said receiving receptacle for receiving and collecting the portion of the syringe barrel severed from the single-use hypodermic needle and the entire needle attached thereto.

7. The apparatus of claim 6 wherein said actuating mechanism further includes a biasing device for reciprocally biasing said knob in a first position wherein said unit is ready to receive the syringe and returning said knob to said first position after said knob has been rotated to a second position to sever the syringe barrel from the syringe.

8. The apparatus of claim 6 wherein said stop has a curvilinear configuration which permits the severed portion of the syringe barrel and the syringe needle attached thereto to pass from the stop into the receiving receptacle upon being severed from the syringe.

9. The apparatus of claim 6 further comprising a disposal cover for removably covering said severing device when said apparatus is not in use and non-removably sealing said severing device when said receiving receptacle is filled and said apparatus is ready for disposal, said disposal cover being configured to be inverted and positioned on said closed end of said receiving receptacle to further stabilize said apparatus when said apparatus is in use.

10. The apparatus of claim 9 wherein said severing device further includes a syringe receptacle cover for sealing said receiving receptacle and positioning said actuating mechanism on said syringe receptacle cover, said syringe receptacle cover being configured to cooperate with said disposal cover for removably receiving said disposal cover when said apparatus is not in use and non-removably sealing said severing device when said receiving receptacle is filled and said apparatus is ready for disposal.

* * * * *